United States Patent [19]

Stock

[11] Patent Number: 4,736,637
[45] Date of Patent: * Apr. 12, 1988

[54] CLEAN BOX

[76] Inventor: James H. Stock, 30805 Old Plank Rd., Wixom, Mich. 48096

[*] Notice: The portion of the term of this patent subsequent to Aug. 4, 2004 has been disclaimed.

[21] Appl. No.: 23,273

[22] Filed: Mar. 9, 1987

Related U.S. Application Data

[62] Division of Ser. No. 858,018, May 1, 1986, Pat. No. 4,683,761.

[51] Int. Cl.[4] ............................................. G01N 1/14
[52] U.S. Cl. ............................. 73/863.83; 73/864.34
[58] Field of Search ............... 73/864, 864.51, 864.81, 73/864.83, 864.91, 863.41, 863.51, 863.52, 863.57, 863.81, 863.86, 864.34, 863.83, 865.6; 312/1, 3; 422/33, 302, 103; 436/176, 174, 180

[56] References Cited

U.S. PATENT DOCUMENTS

| | | | |
|---|---|---|---|
| 937,309 | 10/1909 | Kelly et al. | 312/1 |
| 2,786,740 | 3/1957 | Taylor et al. | 312/1 |
| 3,051,163 | 8/1962 | Trexler | 135/115 |
| 3,536,370 | 10/1970 | Evans et al. | 73/865.6 |
| 3,946,534 | 3/1976 | Egly | 141/11 |
| 4,037,475 | 7/1977 | Topham | 73/863.83 |
| 4,174,632 | 11/1979 | Jansen | 73/864.91 |
| 4,411,157 | 10/1983 | Babin et al. | 73/19 |
| 4,454,773 | 6/1984 | Brunner et al. | 73/863.86 |
| 4,576,918 | 3/1986 | Yeung | 422/103 |
| 4,585,060 | 4/1986 | Bernardin et al. | 73/302 |
| 4,683,761 | 8/1987 | Stock | 73/864.34 |

FOREIGN PATENT DOCUMENTS 2933928  4/1981  Fed. Rep. of Germany ... 73/864.34

Primary Examiner—Stewart J. Levy
Assistant Examiner—Robert R. Raevis
Attorney, Agent, or Firm—Reising, Ethington, Barnard, Perry & Milton

[57] ABSTRACT

A portable apparatus and method for collecting and testing ground water samples including a container (12) defining a chamber (14) in which a control atmosphere is established. A valve means (22) is included which is capable of bypassing water away from the chamber (14) and continuously admitting water samples to the chamber (14). A preferred method of collecting a ground water sample includes the steps of establishing a controlled atmosphere in the chamber (14), directing the flow of water into the chamber (14), collecting the water sample inside the chamber (14), and testing the sample inside the chamber (14) to prevent contamination from the air on the exterior of the chamber (14).

4 Claims, 1 Drawing Sheet

CLEAN BOX

RELATED APPLICATION

This is a divisional of U.S. Ser. No. 858,018, filed May 1, 1986, now U.S. Pat. No. 4,683,761.

TECHNICAL FIELD

This invention relates to an assembly for carrying out processes in a controlled atmosphere. More specifically, the assembly is for collecting and testing a ground water sample under a controlled atmosphere.

BACKGROUND ART

Assemblies for containing controlled atmosphere to perform tests are known in the prior art. Admitting test samples to the controlled atmosphere has been accomplished in a noncontinuous manner. The U.S. Pat. No. 3,536,370 issued to C. G. T. Evans et al discloses a controlled atmosphere assembly wherein a sample is admitted to the controlled atmosphere through a transfer chamber. The Evans apparatus is bulky and not easily moved.

The U.S. Pat. No. 2,786,740 issued to Taylor discloses a portable controlled atmosphere assembly for testing materials. In order to admit materials to be tested into the controlled atmosphere chamber, the chamber wall must be unzipped, and then the materials are placed inside the controlled atmosphere chamber.

The U.S. Pat. No. 937,309 issued to J. J. Kelly et al discloses a photographic chamber to regulate the amount of light inside of the chamber. The patent discloses a method for continuously cycling the liquid through the chamber. The assembly does not include a bypass where the fluid, although still being cycled, can be directed away from the chamber.

SUMMARY OF THE INVENTION AND ADVANTAGES

According to the present invention, there is provided a portable sampling assembly for connection to a ground water pump to collect and test ground water samples. The assembly comprises a container defining a chamber for containing a controlled gaseous medium handling means to manipulate items within the chamber and preventing contamination of the gaseous medium within the chamber by contaminants from the exterior thereof, and a gas inlet and a gas outlet in the container for regulating the flow of the gaseous medium into and out of the chamber. The assembly is characterized by including a valve means having a first position for bypassing a sample of water from the pump away from the chamber to insure that a collected sample is free of pumping system contaminants and a second position allowing for continuous flow of a sample of water into the chamber.

A preferred method of collecting a ground water sample includes the steps of establishing a controlled atmosphere in the chamber by introducing a clean gas to the chamber and then directing the flow of water into the chamber to collect a sample. Once the sample, which is free of outside contaminants, has been collected, it is tested inside the chamber containing the controlled atmosphere.

The present invention offers a system in which water samples can bypass the chamber while being cycled. This insures that the sample collected will be free of all pumping system contaminants. Also, the present invention offers a method to draw a ground water sample directly into a controlled atmosphere, where it can be tested. This prevents outside contamination from entering the ground water sample and effecting testing results.

FIGURES IN THE DRAWING

Other advantages of the present invention will be readily appreciated as the same becomes better understood to the following detailed description when considered in connection with the accompanying drawings wherein.

DETAILED DESCRIPTION OF THE DRAWINGS

Figure 1:
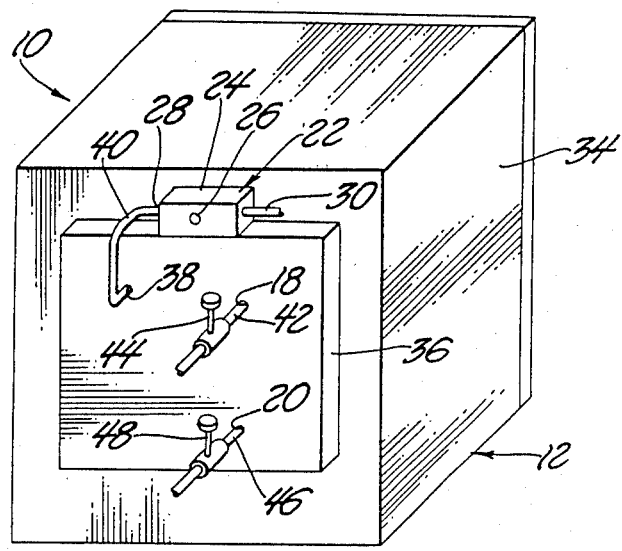
FIG. 1 is a rear perspective view of the preferred embodiment of the invention.
Figure 2:
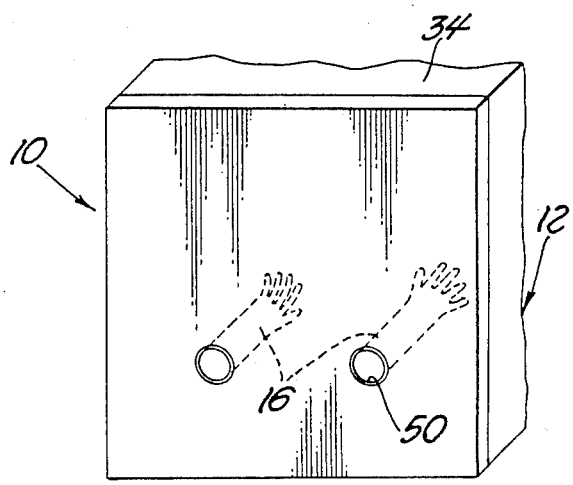
FIG. 2 is a front perspective view partially broken away.
Figure 3:
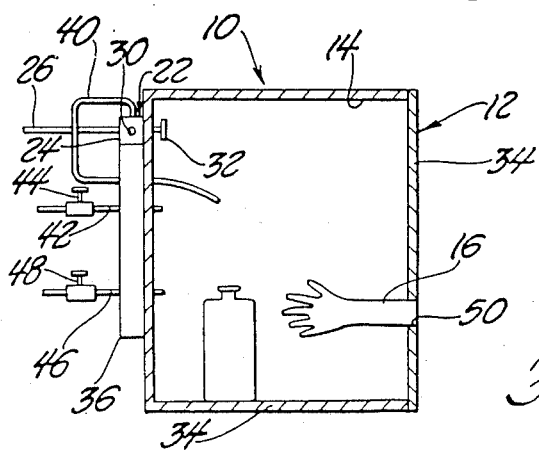
FIG. 3 is a cross-sectional view taken front to back of the preferred embodiment.

A portable ground water sampling assembly for collecting and testing ground water in a controlled atmosphere is generally shown at 10. The assembly includes a container generally shown at 12 which defines a chamber 14 for containing a controlled gaseous medium. A handling means comprising at least one rubber glove 16 is provided to manipulate items within the chamber 14 to prevent contamination of the controlled gaseous medium within the chamber 14 by contaminants from the exterior thereof. The assembly 10 also includes a gas inlet and a gas outlet in the container 12 for regulating the flow of the gaseous medium into and out of the chamber 14. The assembly 10 is characterized by including a valve means generally indicated at 22 having a first position for bypassing a sample of water from the pump (not shown) away from the chamber 14 for allowing water to continuously flow to flush the system to insure that a collected sample of water is free of pumping system contaminants e.g., rust, dirt or air pollutants, and a second position for allowing continuous flow of a sample of water into the chamber 14.

The valve means 22 includes a valve body 24 which has a plurality of channels running through the valve body 24 to allow water to flow through the channels. A first channel 26 defines a bypass for directing water away from the chamber 14. A second channel 28 defines a water outlet to the chamber 14 for allowing continuous water flow into the chamber 14. A third channel 30 defines a water inlet to the valve means 22 for providing water to the valve means 22. The valve means 22 further includes a selector knob 32 for directing the flow of water from the third channel 30 to one of the first and second channels 26 and 28 through the valve body 24. The valve means 22 is attached to the outside of one of the walls 34 of the container 12. The selector knob 32 is disposed within the chamber 14 for directing the flow of water from inside the chamber 14 using the rubber gloves 16 to prevent contamination of the controlled gaseous medium inside the chamber 14. The chamber is hermetically sealed about the shaft supporting the knob 32.

The container 12 is made up of a plurality of walls 34 which hermetically seal the chamber 14. One of the walls 34 contains a reinforcing wall 36 attached to it, providing stability for mounting the valve means 32 to one of the walls 34. All of the walls 34 are transparent for seeing items within the chamber. The wall 34 with the reinforcing wall 36 attached to it includes a water inlet to the chamber 14 comprising an inlet hole 38 through the wall 34 and the reinforcing wall 36 for allowing water to flow through the inlet hole 38. A conduit 40 is provided between the second channel 28 and the water inlet hole 38 defining a passageway for water flow between the second channel 28 and the water inlet hole 38. The conduit 40 extends into the chamber 14 for allowing a water sample to be drawn from the conduit 40.

One of the walls 34 of the container 12 includes a gas inlet comprising a hole 18 through the wall 34. The gas inlet further includes a conduit 42 attached to the hole 18. The conduit 42 has a manually actuated gas inlet valve 44 connected to it for manually regulating the amount of gas flow into the chamber 14.

A gas outlet is also provided. The gas outlet comprises a hole 20 through one of the walls 34 for releasing gas from the chamber 14. The gas outlet further includes a conduit 46 attached to the gas outlet hole 20. The conduit 46 has a manually actuated gas outlet valve 48 connected to it for manually regulating the flow of gas from the chamber 14.

The assembly also includes handling means which comprise at least one rubber glove 16 attached to the periphery of an access opening 50 in one of the walls 34 of the chamber 14. The rubber glove 16 is used to manipulate items within the chamber 14. This prevents contamination of the items within the chamber 14 from contaminants on the exterior of the chamber 14.

To collect the ground water sample, a portable assembly 22 is taken to a site where a pump is connected to the water inlet 30 on the valve means 22. The selector knob 32 is then moved to a position to direct the water to the first channel 26 or the bypass position. The pump is then turned on to allow the water to cycle through the pumping system.

While the water is cycling, a controlled atmosphere is established in the chamber 14 by introducing a clean gas e.g., pure nitrogen or helium to the chamber 14. This is done by manually opening the valve 44 to allow the gas to enter the chamber 14. When pressure has built up inside the chamber 14, the gas inlet valve 44 is closed, the gas outlet valve 48 is opened to relieve the built up pressure. Since the pressure inside the chamber 14 is greater than the external pressure, the gas from chamber 14 will flow out through the outlet conduit 46, and no gas will flow into the chamber 14 through the conduit 46. The gas outlet valve 48 is closed, and the gas inlet valve 44 is then reopened to admit clean gas to the chamber once again. This process of admitting clean gas to the chamber 14 and releasing it through the gas outlet valve 48 is repeated for about one half hour or for any sufficient length of time to ensure that the chamber 14 is purged of all gases, except the clean gas.

Once the controlled atmosphere has been established in the chamber, the selector knob 32 is turned to direct the continuous flow of water samples from the pump into the chamber 14 through the conduit 40. The selector knob 32 is turned by using the rubber glove 16 provided to prevent contamination from the exterior of the chamber 14. The water sample is then collected inside of the chamber 14. Once the water sample has been collected, the selector knob 32 is turned to direct the flow of water to the first channel 26 or bypass position. The collected ground water sample is then tested inside the chamber 14 to prevent contamination from the exterior of the chamber 14.

The invention has been described in illustrative manner and it is to be understood that the terminology which has been used is intended to be in the nature of words of description rather than limitation.

Obviously, many modifications and variations of the present invention are possible in light of the above teachings. It is, therefore, to be understood that within the scope of the appended claims wherein reference numerals are merely for convenience and are not to be in any way limiting, the invention may be practiced otherwise than is specifically described

What is claimed is:

1. A method of collecting ground water samples to test for contamination, said method comprising the steps of: connecting a chamber having a valve thereon to a ground water source, pumping water through the valve and away from the chamber while simultaneously establishing a controlled atmosphere in the chamber by introducing a clean gas to the chamber, and subsequently directing continuous ground water flow into the chamber and collecting a ground water sample in the chamber.

2. A method as set forth in claim 1 further characterized by controlling the flow of water at a position inside the chamber by selecting the channel (26, 40) through which the water will flow.

3. A method as set forth in claim 1 further characterized by testing the ground water sample inside the chamber to prevent contamination from the exterior thereof.

4. A method as set forth in claim 1, further characterized by introducing the clean gas to the chamber by utilizing a process of allowing pressure of the clean gas to build inside the chamber followed by relieving the pressure inside the chamber and repeating the process until the chamber is purged of all gases except the clean gas.

* * * * *